(12) United States Patent
Shimoda et al.

(10) Patent No.: US 8,221,702 B2
(45) Date of Patent: Jul. 17, 2012

(54) SAMPLE DISPENSING APPARATUS AND METHOD

(75) Inventors: Akihiro Shimoda, Hitachinaka (JP); Masahito Kakuno, Naka (JP); Eiji Takaya, Mito (JP); Junichi Oizumi, Kasumigaura (JP)

(73) Assignee: Hitachi-High Technologies Corporation, Tokyo (JP)

( * ) Notice: Subject to any disclaimer, the term of this patent is extended or adjusted under 35 U.S.C. 154(b) by 283 days.

(21) Appl. No.: 12/143,339

(22) Filed: Jun. 20, 2008

(65) Prior Publication Data

US 2008/0317639 A1 Dec. 25, 2008

(30) Foreign Application Priority Data

Jun. 22, 2007 (JP) ................................. 2007-164499

(51) Int. Cl.
*B01L 3/02* (2006.01)

(52) U.S. Cl. ....... 422/527; 422/500; 422/501; 422/68.1; 422/63; 422/65; 73/1.16; 73/1.26; 73/36; 73/1.74; 73/863.25; 73/864; 73/864.01; 73/864.11; 222/55; 222/71; 222/335

(58) Field of Classification Search .................... 422/63, 422/65, 67, 68.1, 500, 509, 501, 527; 73/1.16, 73/1.26, 1.36, 1.74, 863.25, 864.01, 864.11, 73/864; 222/55, 71, 335; 141/18
See application file for complete search history.

(56) References Cited

U.S. PATENT DOCUMENTS

| | | | | |
|---|---|---|---|---|
| 5,540,081 A | * | 7/1996 | Takeda et al. | 73/37 |
| 6,022,747 A | * | 2/2000 | Gherson et al. | 436/69 |
| 7,477,997 B2 | * | 1/2009 | Kaplit | 222/55 |
| 2004/0159675 A1 | * | 8/2004 | Nishino | 222/135 |

FOREIGN PATENT DOCUMENTS

| | | |
|---|---|---|
| JP | 07-027679 | 1/1995 |
| JP | 11-304814 | 11/1999 |

* cited by examiner

*Primary Examiner* — In Suk Bullock
*Assistant Examiner* — Sharon Pregler
(74) *Attorney, Agent, or Firm* — Mattingly & Malur, P.C.

(57) ABSTRACT

A sample dispensing apparatus and method for dispensing a sample such as blood and urine collected for inspection from one vessel to another are provided wherein the remaining quantity of a primary sample can be reduced without disturbing the primary sample. When clogging by a separating agent is detected during suction of a sample such as blood and urine collected for inspection, the sample dispensing apparatus performs raising of an aliquot head such that an opening at the free end of a nozzle tip does not come out of the sample liquid surface to dissolve clogging; sucking of the sample under the residual pressure; and additionally sucking of a fixed quantity of the sample to reduce the remaining quantity of the sample.

10 Claims, 7 Drawing Sheets

SAMPLE DISPENSING APPARATUS AND METHOD

BACKGROUND OF THE INVENTION

1. Field of the Invention

The present invention relates to a sample dispensing apparatus and method. More particularly, it relates to a sample dispensing apparatus for and a method of dispensing a sample by use of a disposable nozzle tip, unloading the dispensed sample to a transfer line, and transferring it to an analyzer or the like.

2. Description of the Related Art

For example, Japanese Patent No. 3410018 describes a dispensing apparatus in which after a sample is sucked by a nozzle tip disposable for each sample therein, the sucked sample is delivered into a secondary sample vessel to automatically dispense a sample such as blood an urine by a certain quantity necessary for analysis and inspection, from one vessel (primary sample vessel) to another (secondary sample vessel). If a sample to be subjected to analysis is a serum constituent, blood containing a separating agent having intermediate specific gravity and high viscosity and stored in the primary sample vessel, is separated into three layers (serum constituent, separating agent, and blood clot constituent) by use of a centrifugal separator. The separating agent is used between the serum constituent and the blood clot constituent to prevent the three layers from being re-mixed. In a sample dispensing apparatus, dispensing is performed to use only the serum constituent for analysis. When the serum constituent in the primary sample vessel is sucked into the nozzle tip by a required quantity, if the quantity of the serum constituent is not sufficient, the opening at the free end of the nozzle tip comes into contact with the separating agent, resulting in clogging. In this case, the serum constituent already sucked when clogging has been detected is delivered to the secondary sample vessel, while it is necessary to decrease the serum constituent left in the primary sample vessel. A relevant technique is disclosed in, for example, JP-A-7-27679. With this technique, if clogging occurs, the serum constituent sucked in the nozzle tip is returned and then re-sucked.

When a sample is sucked, if the quantity of the sample is less than the specified quantity to be sucked, the opening at the free end of the nozzle tip comes into contact with the separating agent before the sample is sucked up as specified, resulting in clogging. Suction is stopped when clogging has been detected and then the sample sucked until detection of the clogging is dispensed into the secondary sample vessel. To decrease the serum constituent remaining in the primary sample, JP-A-7-27679 proposes a technique of returning the serum constituent sucked into the nozzle tip and then re-sucking it if clogging occurs. With this technique, however, since the serum constituent is returned and then re-sucked, it takes much time for processing and the primary sample is disturbed, which may damage the sample.

An object of the present invention is to provide a sample dispensing apparatus and method which dispenses a sample (primary sample) such as blood and urine collected for inspection from one vessel to another, wherein the remaining quantity of a primary sample can be reduced without disturbing of the primary sample.

The above-mentioned object of the present invention can be attained by, when clogging of an opening at the free end of a nozzle tip caused by a separating agent is detected, raising an aliquot head such that the opening at the free end of the nozzle tip does not come out of the liquid surface of serum constituent to dissolve the clogging; sucking the serum constituent under the residual pressure; and additionally sucking a fixed quantity thereof after the residual pressure drops.

In accordance with the present invention, it is possible to decrease the sample that would be left in a primary sample without disturbing the primary sample by raising an aliquot head such that an opening at the free end of a nozzle tip does not come out of the sample liquid surface to dissolve clogging, sucking serum constituent under the residual pressure, and then additionally sucking the same.

DESCRIPTION OF NUMERALS

1 . . . Aliquot head
1a . . . Nozzle base
1b . . . Vacuum suction unit
1c . . . Pressure detector
1d . . . Signal processing circuit
2 . . . Nozzle tip
3 . . . Primary sample vessel
4 . . . Rack for sample vessel transfer
10 . . . Serum
11 . . . Separating agent
12 . . . Blood clot
50 . . . XYZ moving mechanism
100 . . . Dispenser
200 . . . Aliquot control CPU
300 . . . Transfer path control CPU
400 . . . Host CPU

DETAILED DESCRIPTION OF THE PREFERRED EMBODIMENTS

Figure 1:
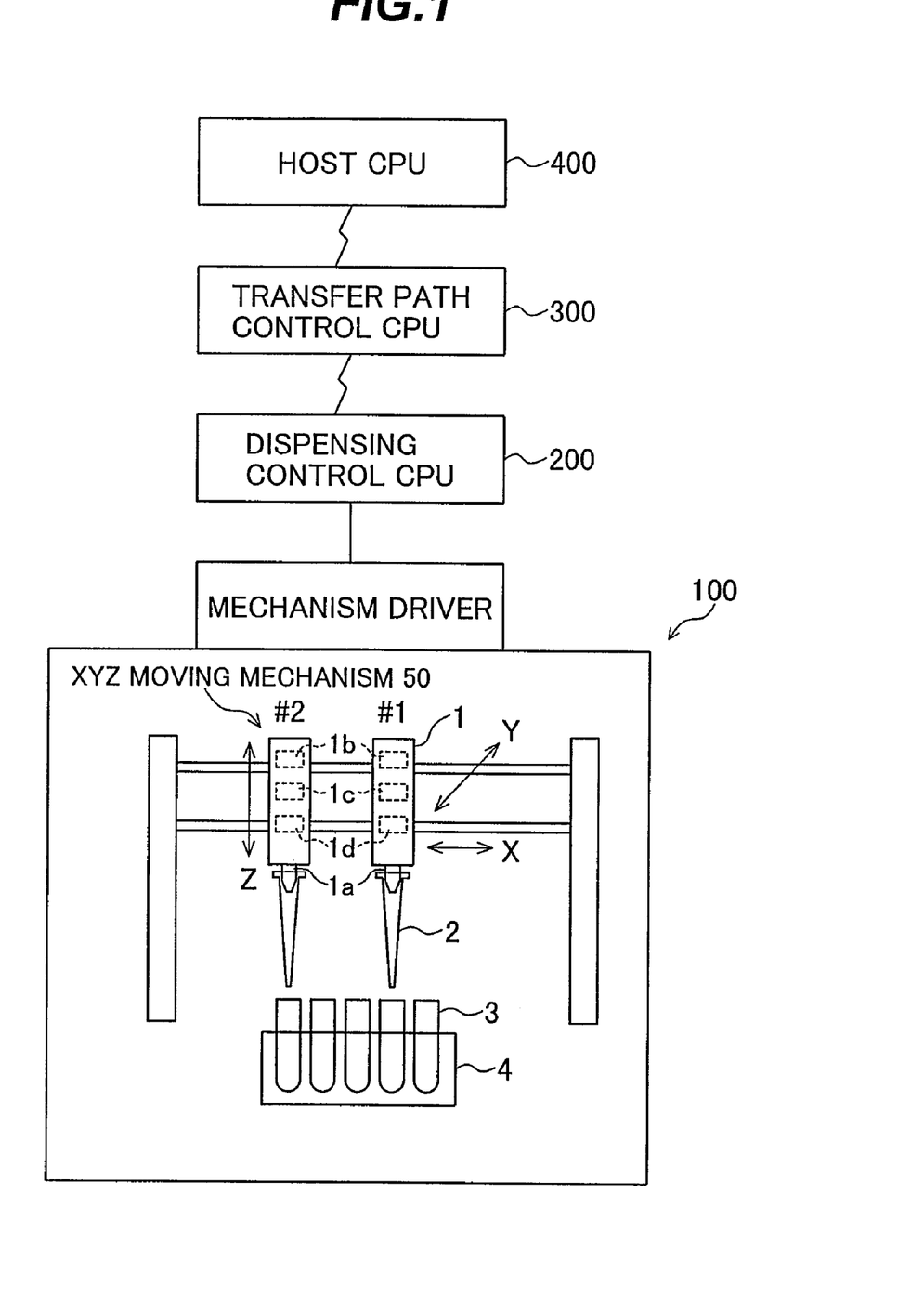
FIG. 1 is a diagram exemplifying the configuration of a sample dispensing apparatus (including a control system) according to the present invention.

An embodiment of the present invention will be explained below with reference to FIGS. 1 to 3. FIG. 1 is a diagram exemplifying the configuration of a sample dispensing apparatus (including a control system). The sample dispensing apparatus includes a dispenser 100, an aliquot control CPU (Central Processing Unit) 200, a transfer path control CPU 300, and a host CPU 400. The dispenser 100 includes an aliquot head 1 and a XYZ moving mechanism 50. A plurality of aliquot heads 1 (#1 and #2 in FIG. 1) are mounted to the XYZ moving mechanism 50 to perform dispensing operation of samples such as serum and urine. The aliquot head 1 is mainly composed of: a nozzle base 1a to which a nozzle tip 2 is attached; a vacuum suction unit 1b which sucks and discharges the sample; a pressure detector 1c which converts pressure change during suction and discharging into an electrical signal; and a signal processing circuit 1d. The sample is sucked and charged from an opening at the free end of the nozzle tip 2. The vacuum suction unit 1b is composed of a pump mechanism including bellows, syringe, etc. (not shown). The signal processing circuit 1d processes an output signal of the pressure detector 1c attached in the aliquot head 1, and the processed signal is sent to the aliquot control CPU 200 for dispensing, failure detection, processing, etc. The host CPU 400, the transfer path control CPU 300, and the aliquot control CPU 200 are connected by a local data communication line. The transfer path control CPU 300 performs transfer control of a sample rack. The aliquot control CPU 200 inquires the host CPU 400 of aliquot information through a rack ID (identification code) and sends aliquot result information thereto. Further, the aliquot control CPU 200 controls dispensing process for the XYZ moving mechanism 50 and the aliquot head 1 of the dispenser 100, and the sample transfer mechanism in the XYZ moving mechanism 50 to perform a series of dispensing operations. The dispensing process to be performed by the aliquot control CPU 200 includes sample suction (to be mentioned later). One or a plurality of primary sample vessels 3 containing a primary sample are mounted on a rack 4 for sample vessel transfer and transferred on a rack basis.

Figure 2A:
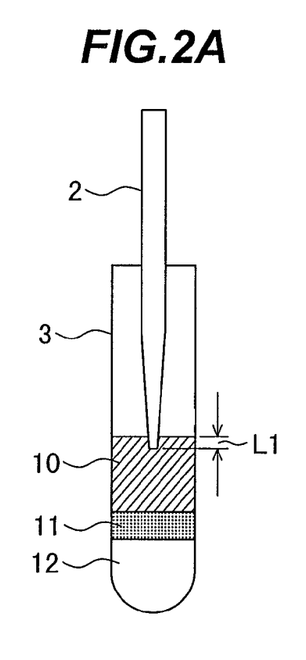
FIGS. 2A to 2E are views showing an embodiment of assistance in explaining the outline of sample suction based on the sample dispensing apparatus.
Figure 2B:
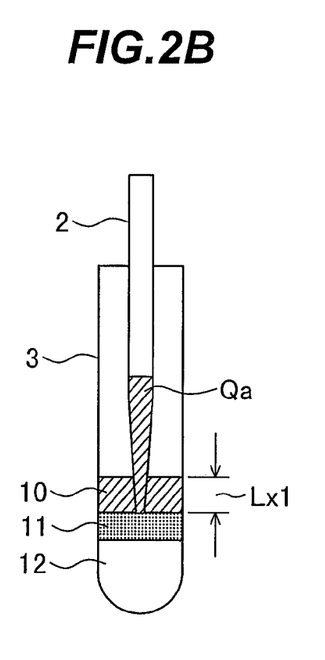
Figure 2C:
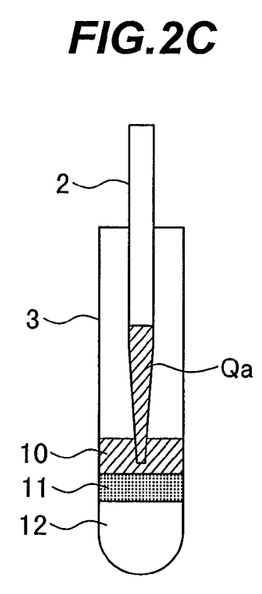
Figure 2D:
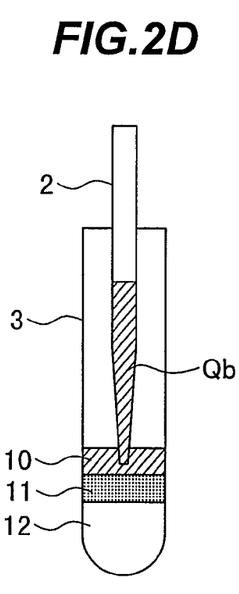
Figure 2E:
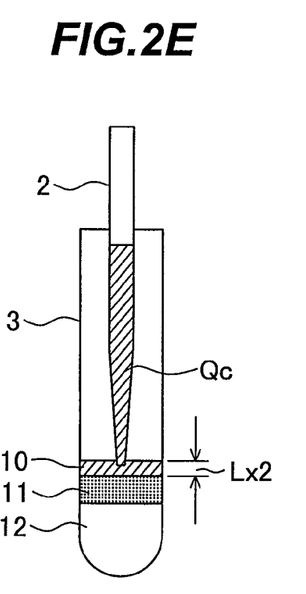

FIGS. 2A to 2E views showing an embodiment of assistance in explaining the outline of sample suction by the sample dispensing apparatus. In FIG. 2A, the nozzle tip 2 is lowered to detect the liquid surface of serum 10. The leading end of the nozzle tip is immersed into the liquid by an amount of immersion L1 specified based on the delay from detection to stop and the sample quantity to be left. In FIG. 2B, the serum 10 is sucked from the detected point and at the same time the nozzle tip 2 is lowered. When the opening at the leading end of the nozzle tip 2 comes into contact with a separating agent 11 and clogging is detected, the lowering operation of the nozzle tip 2 and sample suction are stopped (suction quantity Qa). In this case, the height of the residual quantity of the sample is Lx1. In FIG. 2C, if clogging is detected, the nozzle tip 2 is raised such that the leading end of the nozzle tip 2 does not come out of the liquid surface and clogging is dissolved. In FIG. 2D, when clogging is dissolved, the serum 10 is sucked under the residual pressure in the nozzle tip 2 (suction quantity Qb). In FIG. 2E, when the residual pressure in the nozzle tip 2 disappears, the serum 10 is further sucked and suction is terminated, followed by discharging (suction quantity Qc). The quantity of the left sample becomes Lx2. Here, change in the suction quantities is expressed as Qa<Qb<Qc. It should be noted that once the sample is sucked into the nozzle tip, it is not returned into the primary sample vessel.

Figure 3A:
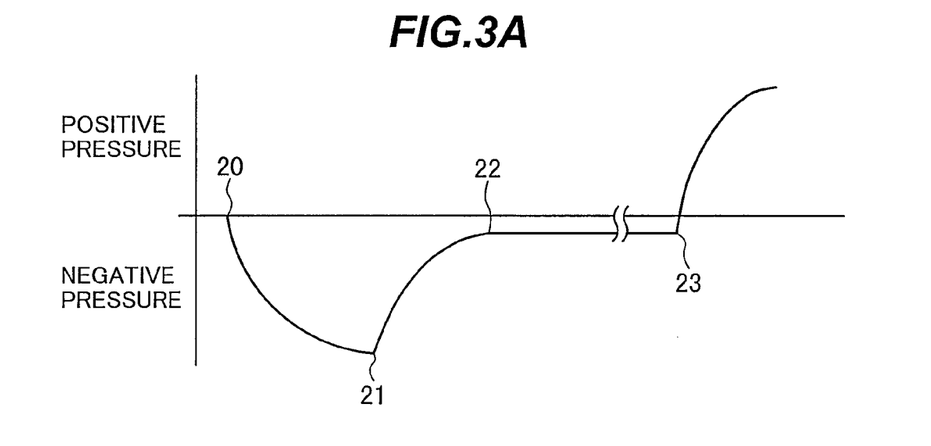
FIGS. 3A to 3C are diagrams exemplifying pressure change in an aliquot head of the sample dispensing apparatus.
Figure 3B:
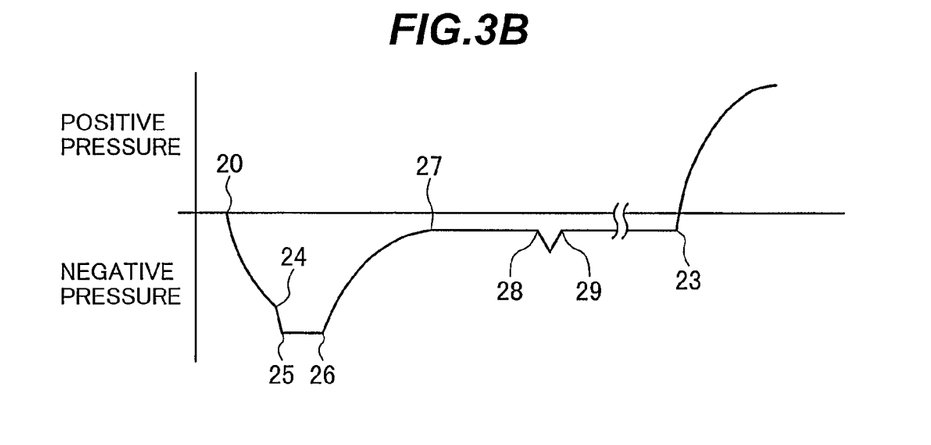
Figure 3C:
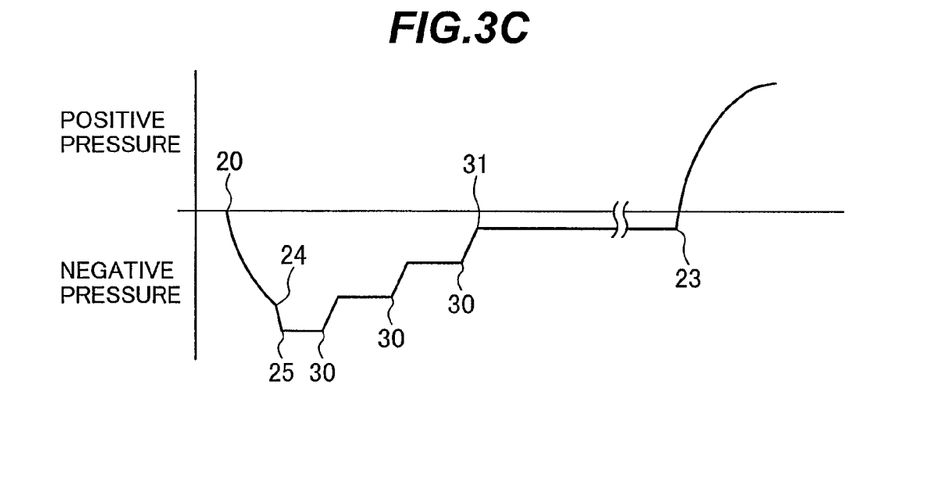

FIGS. 3A to 3C are diagrams exemplifying pressure change in the nozzle tip 2 during suction.

FIG. 3A shows a suction waveform during normal suction. A sample is sucked and discharged by the vacuum suction unit 1b connected with the nozzle tip 2 through an air conduit i.e., the pump mechanism such as bellows and, syringe (not shown, hereinafter represented by bellows). At start-of-suction 20, bellows are expanded to start suction, and suction is performed until completion-of-suction 22 through stop-of-bellows 21. Then, after a certain time period, bellows are contracted at start-of-dispense 23 to start discharging.

FIG. 3B shows a suction waveform when clogging occurs. Suction starts at start-of-suction 20. In response to occurrence-of-clogging 24, bellows are stopped at stop-of-bellows 25 and then the aliquot head 1 is raised to dissolve clogging. Then, since start-of-residual-pressure-suction 26 triggered by the dissolution of clogging until completion-of-residual-pressure 27, suction is performed under the residual pressure in the nozzle tip 2. After the residual pressure in the nozzle tip 2 has decreased, additional suction is performed since start-of-additional-suction 28 until completion-of-additional-suction 29. Then, after a certain time period, the sample is discharged by the sample quantity already sucked when clogging has been detected from start-of-dispense 23, the sample quantity sucked under the residual pressure, and the sample quantity additionally sucked.

FIG. 3C shows a suction waveform in the case where clogging occurs but is not dissolved. After suction is started at start-of-suction 20 and then bellows are stopped at stop-of-bellows 25 in response to occurrence-of-clogging 24, the aliquot head 1 is raised to make an attempt to dissolve clogging. However, if clogging cannot be dissolved, after a certain time period, the residual pressure in the nozzle tip 2 is dissolved by means of discharging-operation 30 (contraction of bellows) for a small quantity of sample. Further, during residual pressure dissolution, the discharge speed is made lower than the normal discharge speed, thus preventing the sample from being dispensed from the nozzle tip 2. If the residual pressure does not decrease at one time, the discharging operation 30 is performed a plurality of times as shown in FIG. 3C. Here, if the nozzle tip 2 is raised from the sample with a residual suction pressure, it sucks air and the air introduced in the nozzle tip 2 rapidly rises. As a result, the aliquot head 1 may be soiled by the sample. Therefore, it is necessary to raise the nozzle tip 2 from the sample after the residual pressure has decreased. When the residual pressure in the nozzle tip 2 disappears at completion-of-residual-pressure-dissolution 31, after a certain time period, sample already sucked when clogging has been detected is dispensed from start-of-dispensing 23.

Figure 4:
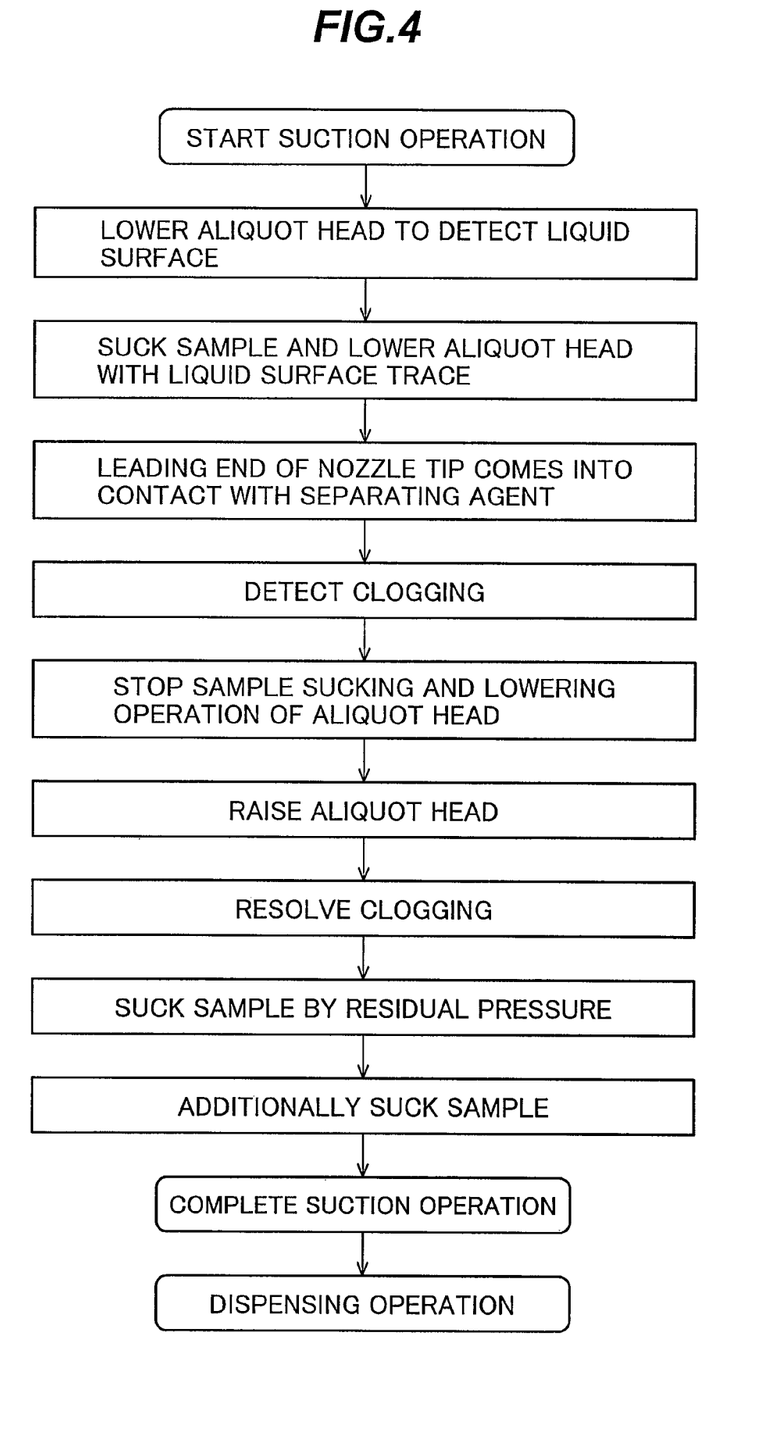
FIG. 4 is a flow chart of suction for the sample dispensing apparatus.

FIG. 4 is a diagram of assistance in explaining the overview of an embodiment of a processing flow chart of suction performed by the aliquot control CPU 200. When suction is started, the aliquot head 1 is lowered and then the opening at the leading end of the nozzle tip 2 reaches the sample liquid surface for surface detection. When the sample liquid surface is detected, the sample is sucked and at the same time the aliquot head is lowered while following the sample liquid surface. If there is not sufficient quantity of primary sample for the specified suction quantity, the opening at the leading end of the nozzle tip comes into contact with the separating agent during sample suction, clogging is detected, and sample suction and the lowering operation of the aliquot head are stopped. Then, the aliquot head is raised such that the opening of the leading end of the nozzle tip does not come out of the surface to dissolve clogging. When clogging is dissolved, the sample is sucked under the residual pressure in the nozzle tip. After the residual pressure in the nozzle tip has decreased, a fixed quantity of sample is additionally sucked, and suction is completed, followed by discharging. The rising distance of the aliquot head and the additional suction quantity after detection of clogging can be separately set from the host CPU or in the dispenser according to the type of aliquot tube used. It should be noted that the additional suction quantity used is the setup value or the quantity calculated by following liquid surface, whichever smaller.

The aliquot control CPU 200 receives a signal from the pressure detector 1c through the signal processing circuit 1d to supervise pressure change in the nozzle tip. The aliquot control CPU 200, based on pressure change in the nozzle tip, performs surface detection, clogging detection, and clogging dissolution detection, etc. For example, pressure change during a period which the opening at the leading end of the nozzle tip reaches the sample liquid surface and sample suction is started is obtained in advance. The pressure change obtained is set as a judgment value. Then, if pressure change detected by the pressure detector $1c$ exceeds the judgment value, the aliquot control CPU 200 judges that the opening at the leading end of the nozzle tip has reached the sample liquid surface. Likewise, pressure change during a period which the opening at the leading end of the nozzle tip comes into contact with a separating agent during sample suction and clogging occurs is obtained in advance. The pressure change obtained is set as a judgment value. Then, if pressure change detected by the pressure detector $1c$ exceeds the judgment value, the aliquot control CPU 200 judges that clogging has occurred. Further, pressure change during a period which clogging is dissolved by raising the nozzle tip is obtained in advance. The pressure change obtained is set as a judgment value. Allowable time limit between the start of elevation of the nozzle tip and the dissolution of clogging is obtained in advance and the pressure change obtained is set. Then, if pressure change detected by the pressure detector $1c$ does not become lower than the judgment value within the allowable time limit, the aliquot control CPU 200 judges that clogging has not been dissolved; otherwise, it judges that clogging has been dissolved.

Further, the aliquot control CPU 200 outputs a drive instruction in the Z-axis direction (vertical direction) to the XYZ moving mechanism 50 to control the amount of movement in the Z-axis direction of the XYZ moving mechanism 50 and control the amount of movement in the Z-axis direction of the nozzle tip 2. At the same time, the aliquot control CPU 200 outputs a drive instruction to the vacuum suction unit 1b to control the amount of movement of the bellows of the vacuum suction unit 1b thus controlling the suction quantity of the nozzle tip 2. Based on the preset amount of movement in the Z-axis direction of the nozzle tip 2 necessary for suction and the amount of movement of the bellows, the aliquot control CPU 200 generates and outputs a drive instruction in the Z-axis direction to the XYZ moving mechanism 50 and a drive instruction to the vacuum suction unit 1b.

Figure 5:
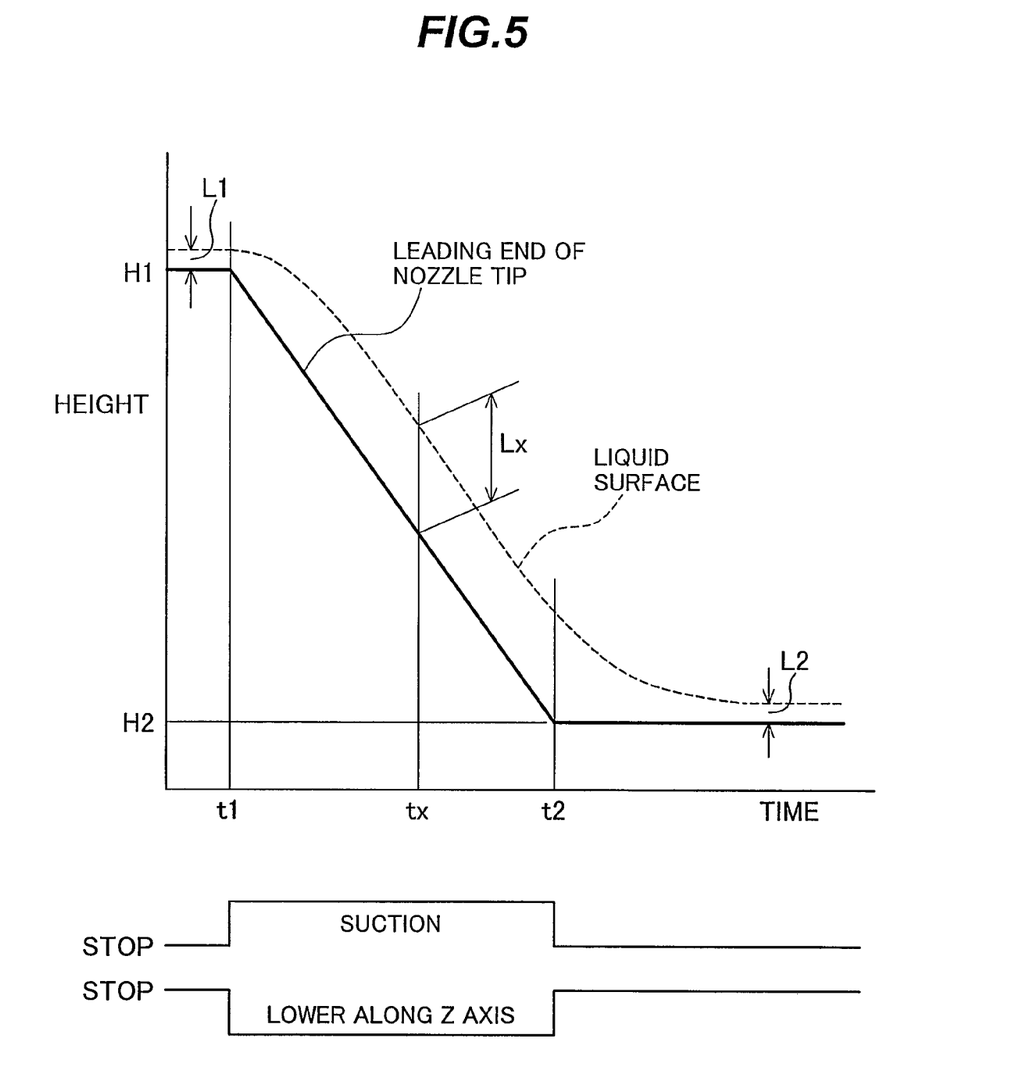
FIG. 5 is a diagram showing a relation between a nozzle tip and height of a sample liquid surface during normal suction operation based on the sample dispensing apparatus.

FIG. 5 is a diagram showing a relation between a nozzle tip and height of a sample liquid surface during normal suction operation according to the present invention. After liquid surface detection, the nozzle tip 2 is immersed into the sample liquid surface by L1 (at a height position H1) and then suction is started from time t1. The sample liquid surface is lowered almost on a first-order lag basis from the lowering operation of the leading end of the nozzle tip 2. Settings are set such that time it takes for suction is the same as that for the operation of the nozzle tip 2; operation proceeds between t1 and t2 (at a height position H2).

At time tx, a following error between the sample liquid surface and the leading end of the nozzle tip 2 becomes a value indicated at Lx. To prevent the leading end of the nozzle tip 2 from coming out of the sample during suction resulting in air suction, a relation Lx≧L1 must be satisfied. At time t2 and later, the sample is sucked under the residual pressure caused by suction delay and the remaining sample quantity becomes a value indicated at L2. The nozzle tip 2 is lowered so that L2 substantially equals L1. L1 (≈L2) denotes the quantity of the primary sample that has been left. L1 can be set in milliseconds as the quantity of the primary sample to be stored for re-inspection.

Figure 6:
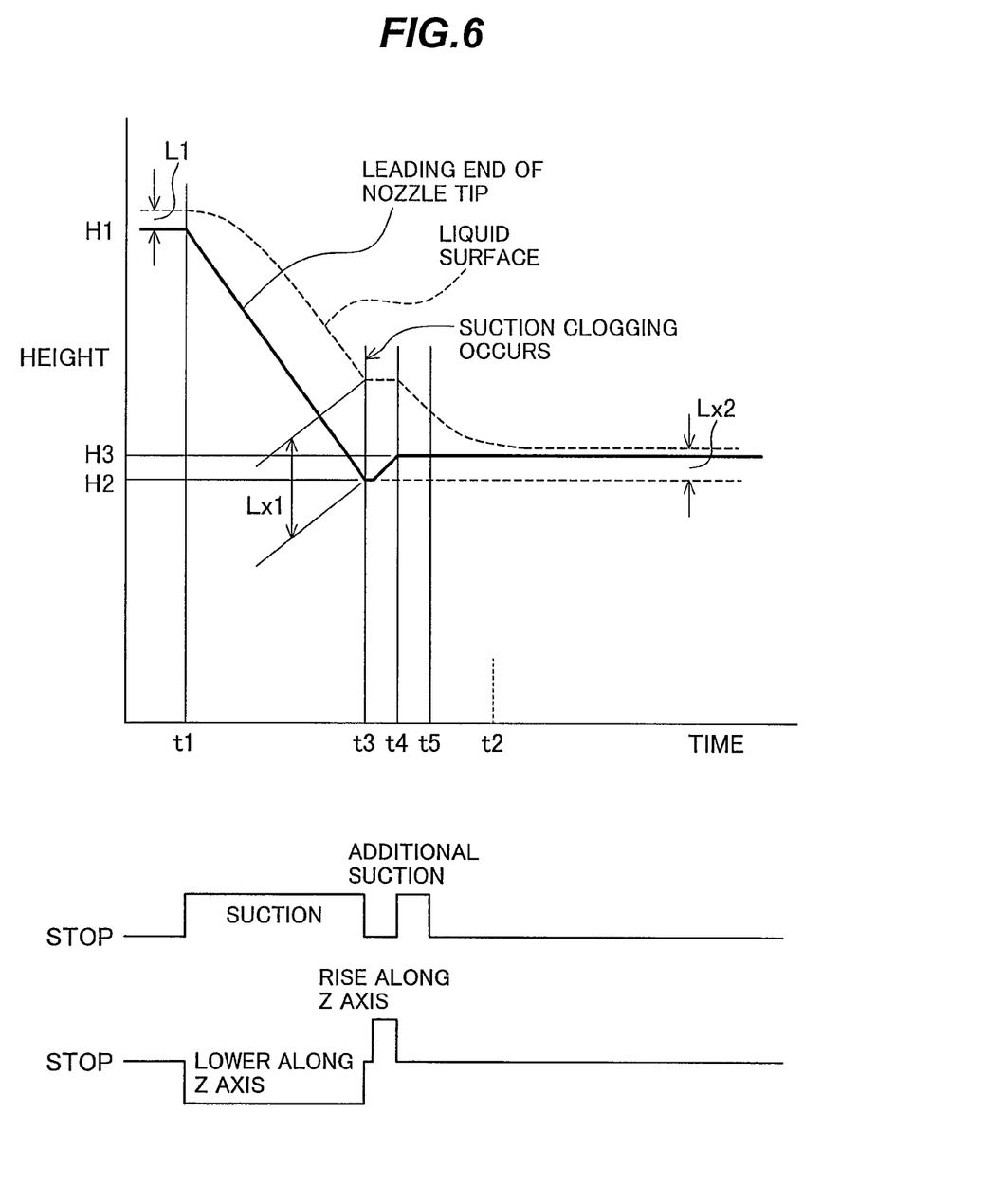
FIG. 6 is a diagram showing a relation between the nozzle tip and height of the sample liquid surface during operation performed when suction clogging occurs based on the sample dispensing apparatus.

FIG. 6 is a diagram showing a relation between the nozzle tip 2 and the sample liquid surface when suction clogging occurs. After surface detection, the nozzle tip 2 is immersed into the sample liquid surface by L1 (at the height position H1) and then suction is started from time t1. When the leading end of the nozzle tip 2 reaches a separating agent at time t3 (at the height position H2 of the leading end of the nozzle tip) and then the suction opening at the leading end is blocked, suction clogging is detected and the lowering operation of the nozzle tip 2 and suction are stopped. With suction stopped, the nozzle tip 2 is raised (at a height position H3) such that the opening does not come out of the sample between t3 and t4. When the leading end of the nozzle tip 2 is separated from the separating agent and clogging is dissolved between t3 and t4, the sample is sucked under the residual pressure. Further, when additional suction is performed between t4 and t5, the quantity of the sample left becomes a value indicated at Lx2. The amount of elevation of the nozzle tip 2 between t3 and t4 (H3 to H2) and the additional suction quantity between t4 and t5 (quantity equivalent to Lx1 to Lx2) are optimized, so that the sample quantity to be left suffices a portion of the sample associated with the elevation of the nozzle tip 2. Lx1 is obtained through calculation from H1, H3, vessel shape (inner diameter, taper, etc.), the suction quantity Qa between t1 and t3. Then, the amount of elevation of the nozzle tip 2 (H3 to H2) and the additional suction quantity (Lx1 to LX2) are calculated. The quantity of the sample that is left is problematic in the case of separate dispensing, where it is desirable to set Lx2 to zero. When suction is balanced with the surface tension of the sample in suction under the residual pressure after time t5 and later, it is possible to further reduce the quantity of the sample to be left without performing air suction.

When priority is given to the quantity of the sample to be left in the primary sample for its storage, it is preferable to set Lx2 to the setting of the amount of immersion L1 for storage.

Figure 7:
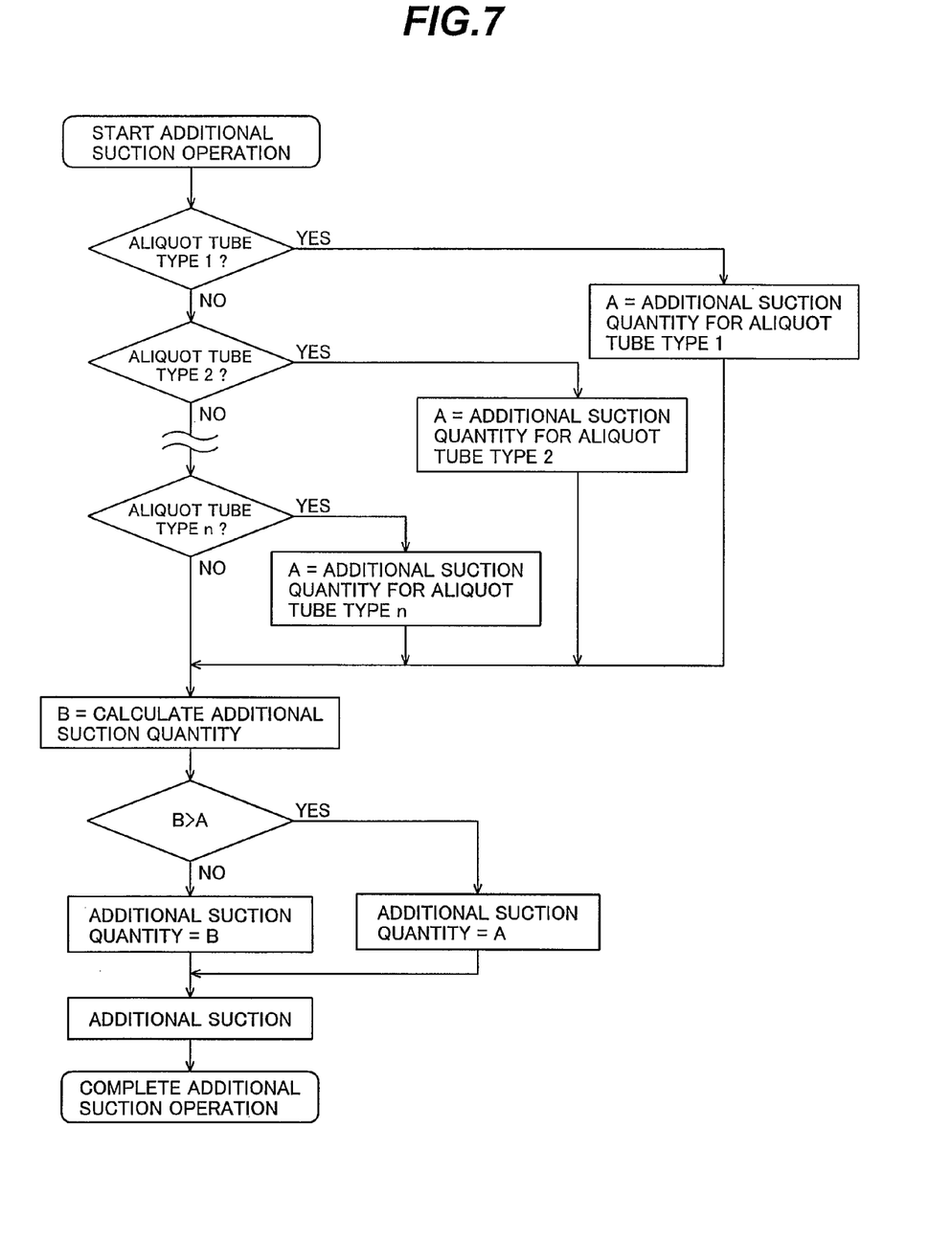
FIG. 7 is a flow chart for judging the additional suction quantity when suction clogging occurs based on the sample dispensing apparatus.

FIG. 7 is a diagram showing a judgment processing flow for calculating the additional suction quantity according to the present invention performed by the aliquot control CPU 200. When additional suction is performed, based on the additional suction quantity set for each type of aliquot tube used, the additional suction quantity of the type of aliquot tube currently performing processing is set as the additional suction quantity A. The additional suction quantity obtained by being calculated or tabled from coordinate values of the height of the leading end of the nozzle tip at which clogging was detected and from the suction quantity accumulated up to suction clogging occurrence, is regarded as an additional suction quantity B. The table is stored in a memory. The additional suction quantity A is compared with the quantity of additional suction B, and additional suction is performed regarding the value whichever smaller as the additional suction quantity.

FIG. 7 is a processing flow chart in the case where the quantity of additional suction A obtained from the type of primary sample vessel, and the additional suction quantity B obtained through calculation or a table stored in memory from the suction clogging position and the suction quantity up to suction clogging occurrence, is regarded as a final additional suction quantity. Further, it is also possible to variably set a user-input suction quantity not involving air suction as a additional suction quantity C, and regard the additional suction quantities A to C, whichever smallest, as a final additional suction quantity. User input can be made using, for example, input means for the host CPU 400 (keyboard, etc.). Further, FIG. 7 is a flow chart for judging the additional suction quantity. Likewise, the amount of elevation of the nozzle tip 2 may be separately set in association to the type of aliquot tube used as a primary sample.

The above-mentioned method can reduce the remaining quantity of a sample without discharging the sample once sucked into the nozzle tip (without disturbing the primary sample in the vessel 3).

What is claimed is:

1. A sample dispensing apparatus for dispensing a serum constituent contained in a primary sample wherein the apparatus comprises:
    an aliquot tube containing a blood clot constituent, a separating agent, and a serum constituent,
    a disposable nozzle tip;
    a moving mechanism which vertically moves the nozzle tip;
    a suction unit which generates a negative pressure for suction at the nozzle tip;
    a pressure sensor which detects the pressure in the nozzle tip; and
    an aliquot control unit which controls the moving mechanism and the suction unit based on a value detected by the pressure sensor and is configured to preform suction of the serum constituent in the primary sample while lowering the nozzle tip;
    said aliquot control unit configured to contain a judgment value wherein said judgment value comprises:
    a preset pressure change provided when a leading end of the nozzle tip becomes clogged when contacted with the separating agent during sample suction,
    wherein when the pressure change detected by the pressure detector exceeds the judgment value when contacted with the separating agent, the aliquot control unit raises the nozzle tip to dissolve the clogging at an opening at a leading end of the nozzle tip without discharging the serum constituent previously sucked into the nozzle tip;
    and said aliquot control unit supervises a residual pressure in the nozzle tip with the pressure sensor to judge clogging of the opening at the leading end of the nozzle tip which is to be dissolved.

2. The sample dispensing apparatus according to claim 1, wherein the aliquot control unit further is configured to control the moving mechanism and the suction unit to perform, after the dissolution of clogging re-suction of, additional sucking of a serum constituent remaining in the primary sample.

3. The sample dispensing apparatus according to claim 1, wherein:
    the aliquot control unit further is configured to variably set the amount of elevation of the nozzle tip after detection of clogging to a value that falls within a range where clogging by the separating agent can be dissolved and the opening at the leading end of the nozzle tip does not come out of the sample liquid surface.

4. The sample dispensing apparatus according to claim 1, wherein the aliquot control unit further is configured to control the moving mechanism and the suction unit to perform, when clogging by the separating agent is not dissolved after the nozzle tip is raised, discharging of a small quantity of sample.

5. The sample dispensing apparatus according to claim 1, wherein the aliquot control unit further is configured to control the moving mechanism and the suction unit to perform, when clogging by the separating agent is not dissolved after the nozzle tip is raised, discharging of a small quantity of sample at a discharge speed lower than the normal discharge speed.

6. The sample dispensing apparatus according to claim 2, wherein the aliquot control unit is configured to obtain the quantity to be additionally sucked based on the type of primary sample vessel and a calculation or table stored in a memory from a suction clogging position and a suction quantity accumulated up to the occurrence of suction clogging.

7. The sample dispensing apparatus according to claim 6, wherein the aliquot control unit further is configured to set the additional suction quantity to a quantity not involving air suction by a user-input.

8. The sample dispensing apparatus according to claim 6, wherein the aliquot control unit is configured to regard the quantity obtained from the type of primary sample vessel, and the quantity obtained by the calculation or table stored in the memory from the suction clogging position and the suction quantity accumulated up to suction clogging occurrence, whichever is smaller, as the additional suction quantity.

9. The sample dispensing apparatus according to claim 7, wherein the aliquot control unit is configured to regard the quantity obtained from the type of primary sample vessel, the quantity obtained by the calculation or table stored in the memory from the suction clogging position and the suction quantity accumulated up to suction clogging occurrence, and the quantity not involving air suction set by a user-input, whichever is smallest, as the additional suction quantity.

10. The sample dispensing apparatus according to claim 8, wherein the aliquot control unit further is configured to separately set the amount of elevation of the nozzle tip and the additional suction quantity upon clogging detected, in association with the type of aliquot tube used as a primary sample.

* * * * *